United States Patent
Gallegos

[19]

[11] Patent Number: 6,080,139
[45] Date of Patent: Jun. 27, 2000

[54] APPARATUS FOR PROTECTING CARE PROVIDERS FROM BABY URINATION ACCIDENTS

[76] Inventor: Vicki Gallegos, 6155 Fairlane Dr., Oakland, Calif. 94611

[21] Appl. No.: 08/833,581

[22] Filed: Apr. 7, 1997

[51] Int. Cl.⁷ .............................. A61F 13/15; A61F 13/20
[52] U.S. Cl. ..................... 604/387; 604/358; 604/385.1; 2/1; 2/403; 450/81
[58] Field of Search ................... 604/348, 355, 604/356, 352, 358, 385.1, 386, 387, 389; 450/81, 37; 2/1, 403

[56] References Cited

U.S. PATENT DOCUMENTS

| | | | |
|---|---|---|---|
| D. 344,210 | 2/1994 | Cousins et al. | D7/503 |
| D. 362,594 | 9/1995 | McEntee | D7/538 |
| 2,553,825 | 5/1951 | Langs | 450/81 |
| 2,877,769 | 3/1959 | Hill . | |
| 2,891,544 | 6/1959 | London | 450/37 |
| 3,227,162 | 1/1966 | Aguirre . | |
| 3,356,090 | 12/1967 | Planting et al. | 450/37 |
| 3,406,690 | 10/1968 | Igel . | |
| 3,626,943 | 12/1971 | Worcester | 604/348 |
| 3,749,102 | 7/1973 | Wynants | 450/81 |
| 3,858,584 | 1/1975 | Johnson . | |
| 3,964,111 | 6/1976 | Packer | 604/355 |
| 4,074,721 | 2/1978 | Smits et al. | 450/37 |
| 4,164,228 | 8/1979 | Weber-Unger | 450/37 |
| 4,333,471 | 6/1982 | Nakai | 450/81 |
| 4,566,458 | 1/1986 | Weinberg | 2/1 |
| 4,601,716 | 7/1986 | Smith . | |
| 4,700,699 | 10/1987 | Tollerud et al. | 604/358 |
| 4,731,063 | 3/1988 | Newkirk . | |
| 4,886,509 | 12/1989 | Mattsson . | |
| 5,248,307 | 9/1993 | Sokoloff . | |
| 5,695,485 | 12/1997 | Duperret et al. | 604/349 |
| 5,702,381 | 12/1997 | Cottenden | 604/385.1 |
| 5,782,672 | 7/1998 | Woodley | 450/81 |

FOREIGN PATENT DOCUMENTS

| | | | |
|---|---|---|---|
| 0191004 | 8/1986 | European Pat. Off. | 604/385.1 |
| 2577798 | 8/1986 | France | 604/385.1 |
| 2064961 | 6/1981 | United Kingdom | 604/385.1 |
| 8605387 | 9/1986 | WIPO | 604/385.1 |

*Primary Examiner*—Mark O. Polutta
*Attorney, Agent, or Firm*—Gary R. Jarosik; Michael A. Carrillo

[57] ABSTRACT

An apparatus for protecting care providers from baby urination accidents. The apparatus includes a generally domed shaped, contiguous shell terminating in a base wherein the shell and base are sized such that the genitalia of a baby is accomodated and covered in the immediately surrounding region. The base is weighted to provide the apparatus with a center of gravity proximate to the baby when disposed over the genitalia thereof to provide the apparatus with stability when positioned as desired. An optional adhesive layer may be provided to the base to further the stability of the apparatus.

9 Claims, 1 Drawing Sheet

APPARATUS FOR PROTECTING CARE PROVIDERS FROM BABY URINATION ACCIDENTS

BACKGROUND OF THE INVENTION

This invention relates generally to protective devices and, more particularly, relates to an apparatus for protecting care providers from baby urination accidents.

As those who have cared for babies will appreciate, during times when the genitalia is exposed, such as during diaper changes, medical examinations, etc., there exists the risk that urination accidents will occur. These urination accidents, while being generally unpleasant to experience, also have the undesirable tendency to result in the soilage of the clothes of the care provider. Accordingly, care providers typically desire to limit the time the genitalia are exposed for purposes of minimizing the risk of such accidents. While minimizing the time of exposure of the genitalia may work in some instances in reducing the noted risks, there does exist instances when the baby is required to be undressed for a lengthy period of time, such as during medical examinations, treatment, weighing, etc. Accordingly, other forms for minimizing the risk of such urination accidents have developed.

For example, care providers often attempts to cover the genitalia with a spare diaper or cloth during the diaper changing and cleaning process. However, covering the genitalia with a spare diaper or cloth is seen to be less than effective as leg movements of a baby often results in the covering being kicked off. Furthermore, attempts by the care provider to hold the covering in place is seen to limit the ability of the care provider to effectuate the desired operation as one hand is necessarily dedicated to maintaining the covering in the desired location. Accordingly, it is seen that a need exists for an improved means for protecting care providers from baby urination accidents.

As a result of this existing need, it is an object of the present invention to provide an apparatus for use in protecting care providers from baby urination accidents.

It is a further object of the present invention to provide a protective device capable of maintaining its desired positioning on a baby without requiring further intervention on the part of the care provider.

It is another object of the present invention to provide a protective device which may be easily manufactured either as a disposable product or a reusable product.

SUMMARY OF THE INVENTION

In accordance with the present invention, an apparatus for protecting care providers from baby urination accidents is provided. The apparatus includes a generally domed shaped, contiguous shell terminating in a base wherein the shell and base are sized such that the genitalia of a baby is accomodated and covered in the immediately surrounding region. The base is preferably weighted to provide the apparatus with a center of gravity proximate to the baby when disposed over the genitalia thereof to provide the apparatus with stability when positioned as desired. An optional adhesive layer may be provided to the base to further the stability of the apparatus.

A better understanding of the objects, advantages, features, properties and relationships of the invention will be obtained from the following detailed description and accompanying drawings which set forth illustrative embodiments which are indicative of the various ways in which the principles of the invention may be employed.

BRIEF DESCRIPTION OF THE DRAWINGS

For a better understanding of the invention, reference may be had to the preferred embodiments shown in the following drawings in which.

DETAILED DESCRIPTION

Figure 1:
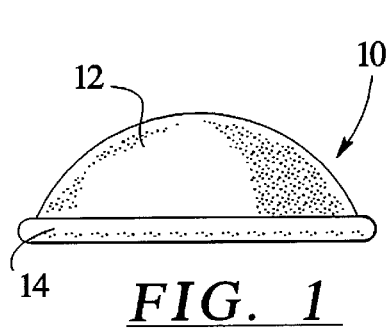
FIG. 1 illustrates a side view of a first embodiment of the apparatus which is the subject of the present invention.
Figure 3:
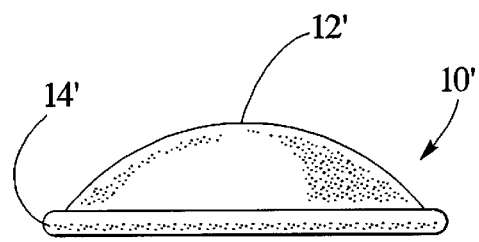
FIG. 3 illustrates a side view of a second embodiment of the apparatus.
Figure 4:
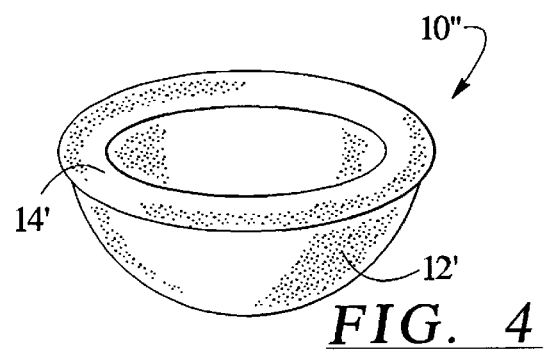
FIG. 4 illustrates a perspective view of the top and side of the apparatus illustrated in FIG. 3.
Figure 2:
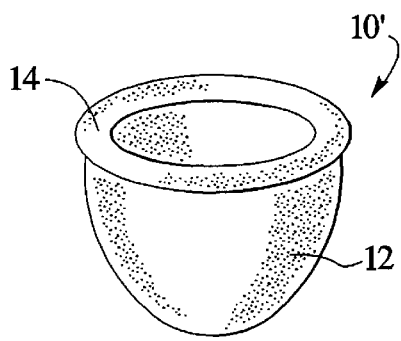
FIG. 2 illustrates a perspective view of the top and side of the apparatus illustrated in FIG. 1.
Figure 6:
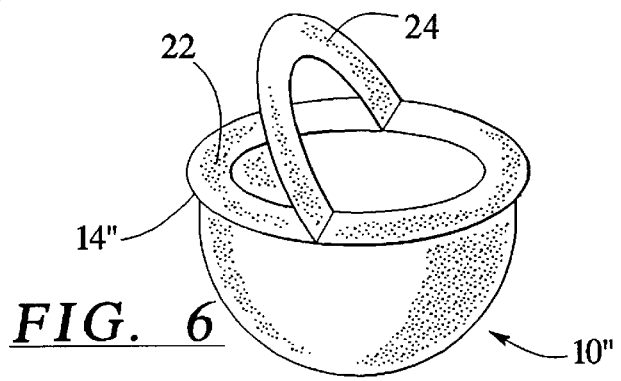
FIG. 6 illustrates a perspective view of the top and side of another embodiment of the apparatus.
Figure 5:
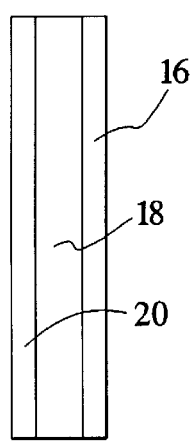
FIG. 5 illustrates a cross section view of a further embodiment of the apparatus.
Figure 7:
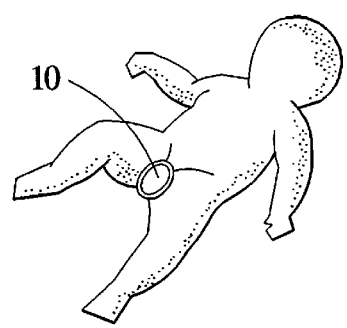
FIG. 7 illustrates the apparatus of FIG. 1 being used in connection with a baby.
Figure 8:
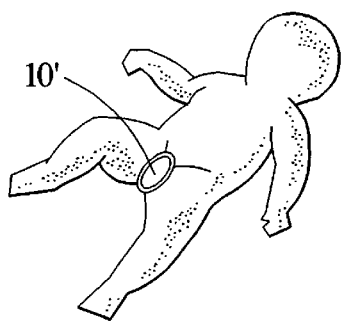
FIG. 8 illustrates the apparatus of FIG. 3 being used in connection with a baby.

Referring now to the figures, wherein like reference numerals refer to like elements, there is generally illustrated in FIGS. 1–8 apparatuses for protecting a care provider from baby urination accidents. Specifically, a first embodiment of the protective device 10, illustrated in FIGS. 1–2, may be described as having a generally domed shaped, contiguous shell 12 terminating in a substantially circular base 14. A second embodiment of the protective device 10', illustrated in FIGS. 3–4, may be described as having a generally domed shaped, contiguous shell 12' terminating in a substantially oblong-shaped base 14'. As will be understood, the protective device 10' having the substantially oblong-shaped base 14' is especially well suited for use in connection with male babies. The height of the shell 12/12' and the diameters/lengths of the base 14/14' are preferably sized such that the genitalia is accomodated and covered in the immediately surrounding region. In this manner, as illustrated in FIGS. 7–8, the size of the device allows it to be positioned over the genitalia whereby the device avoids substantial contact with the upper legs of a baby. As a result, the size of the device allows the device to generally avoid the problems associated with the prior art, namely, the unwanted exposure of the covered area caused by movements of the legs of the baby.

To further assist in the prevention of a change in the positioning of the protective device 10/10', the base 14/14' is preferably weighted. In this manner, the center of gravity of the protective device 10/10' is lowered to a location which is more proximate to the body of the baby. This positioning of the center of gravity is seen to provide the device with greater resistance to inadvertent movement which is typically caused by the movement of the upper legs of a baby. In the preferred embodiment of the invention, the weighting of the base 14/14' is accomplished by providing the base 14/14' with a greater thickness of material than that provided to the shell 12/12', for example, by doubling or causing the successive overlapping of the base material. While this method of weighting the protective device 10/10' is preferred, those skilled in the art will appreciate that other forms of weighting the base 14/14' may be utilized without departing from the spirit of the subject invention.

The shell 12/12' may be constructed from 100% cotton or other like types of absorptive, cloth like materials when the protective device 10/10' is manufactured to be reusable and washable. In the preferred embodiment, the shell 12/12' would have a thickness of approximately ¼ inch. In a further embodiment of the invention, illustrated in FIG. 5, the shell 12/12' may also be constructed to include an outer layer 16 of moisture resistant material, a middle layer 18 of moisture absorbent material, and an inner layer 20 of moisture wicking material. The protective device 10/10' constructed in accordance with this embodiment will typically be disposed after usage.

In a further embodiment of the protective device 10" may further be provided with a mildly adhesive surface 22 carried on the base 14" thereof for purposes of further preventing the inadvertent movement of the device. As illustrated in FIG. 6, the protective device 10" may be coated with the adhesive surface 22, which may be a petrolatum-based gel or other suitable form of mild adhesive, and covered with a removable cover 24 at the time of manufacture. In this manner, the care provider need only remove the cover 24 to expose the adhesive surface 22 prior to positioning the protective device 10" over the genitalia whereby the mating of the adhesive layer with the skin of the baby will function to further stabilize the protective device in its desired position. This embodiment of the subject invention lends itself particularly well to the medical environment where longer periods of protection may be needed and the baby is more prone to movement.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any equivalent thereof.

What is claimed is:

1. An apparatus for protecting care providers from baby urination accidents comprising:

a generally domed shaped, contiguous, absorbent shell terminating in a generally oblong-shaped circular base wherein the shell and base are sized such that the genitalia of a baby is accommodated and covered in the immediately surrounding region, wherein the shell includes an inner layer and an outer layer, said outer layer comprising a moisture resistant material, wherein the base carries an adhesive, wherein the apparatus is provided with a center of gravity proximate to the baby when disposed over the genitalia thereof and wherein the base is weighted.

2. The apparatus as recited in claim 1, wherein the base is provided with a thickness greater than that provided to the shell.

3. The apparatus as recited in claim 1, wherein the shell comprises an absorbant, washable material.

4. The apparatus as recited in claim 3, wherein the absorbant, washable material comprises cotton.

5. The apparatus as recited in claim 1, wherein said inner layer comprises a wicking material and an intermediate layer of absorptive material.

6. An apparatus for protecting care providers from baby urination accidents comprising:

a generally domed shaped, contiguous shell terminating in a base wherein the shell and base are sized such that the genitalia of a baby is accomodated and covered in the immediately surrounding region, wherein the base is weighted to provide the apparatus with a center of gravity proximate to the baby when disposed over the genitalia thereof, wherein the shell comprises an outer layer of moisture resistant material, an inner layer of wicking material, and an intermediate layer of absorptive material, and wherein the base carries an adhesive.

7. The apparatus as recited in claim 6, wherein the base is provided with a generally circular shape.

8. The apparatus as recited in claim 6, wherein the base is provided with a generally oblong shape.

9. The apparatus as recited in claim 6, wherein the thickness of the base is greater that that provided to the shell.

* * * * *